United States Patent
Harris

(10) Patent No.: US 9,717,653 B2
(45) Date of Patent: Aug. 1, 2017

(54) CONDUCTIVE GRID SENSOR FOR SMART PACKAGING

(71) Applicant: Vatex Explorations, LLC, Grapevine, TX (US)

(72) Inventor: James Wayne Harris, Grapevine, TX (US)

( * ) Notice: Subject to any disclaimer, the term of this patent is extended or adjusted under 35 U.S.C. 154(b) by 17 days.

(21) Appl. No.: 14/620,792

(22) Filed: Feb. 12, 2015

(65) Prior Publication Data

US 2015/0228178 A1 Aug. 13, 2015

Related U.S. Application Data

(60) Provisional application No. 61/939,108, filed on Feb. 12, 2014.

(51) Int. Cl.
| | | |
|---|---|---|
| *A61J 7/02* | (2006.01) | |
| *A61J 1/03* | (2006.01) | |
| *A61J 7/00* | (2006.01) | |
| *A61J 7/04* | (2006.01) | |
| *G06F 19/00* | (2011.01) | |

(52) U.S. Cl.
CPC ............ *A61J 7/02* (2013.01); *A61J 1/035* (2013.01); *A61J 7/0076* (2013.01); *A61J 7/0436* (2015.05); *G06F 19/3462* (2013.01)

(58) Field of Classification Search
CPC .................................... A61J 7/02; A61J 1/035
USPC ........................................................ 340/541
See application file for complete search history.

(56) References Cited

U.S. PATENT DOCUMENTS

| | | | |
|---|---|---|---|
| 1,387,072 A | 8/1921 | Putnam | |
| 6,244,462 B1 * | 6/2001 | Ehrensvard | A61J 1/035 221/25 |
| 7,113,101 B2 | 9/2006 | Petersen et al. | |
| 7,178,417 B2 | 2/2007 | Petersen et al. | |
| 2009/0065522 A1 * | 3/2009 | Benouali | A61J 1/035 221/7 |

* cited by examiner

*Primary Examiner* — Qutbuddin Ghulamali
(74) *Attorney, Agent, or Firm* — Richards Patent Law P.C.

(57) ABSTRACT

A blister packaging including a blister card including a plurality of flexible blisters; and a backing sheet including blister backing portions and backing securing portions, wherein when the backing securing portions are secured to the blister card, the blister backing portions are aligned to each blister forming a plurality of compartments adapted to store a medicament, and wherein the backing includes two or more conductive first leads affixed to the backing, two or more conductive second leads affixed to the backing, and a plurality of conductive zones, wherein each conductive zone electrically connects one of the first leads to one of the second leads, and wherein each blister backing portion includes a conductive zone.

19 Claims, 2 Drawing Sheets

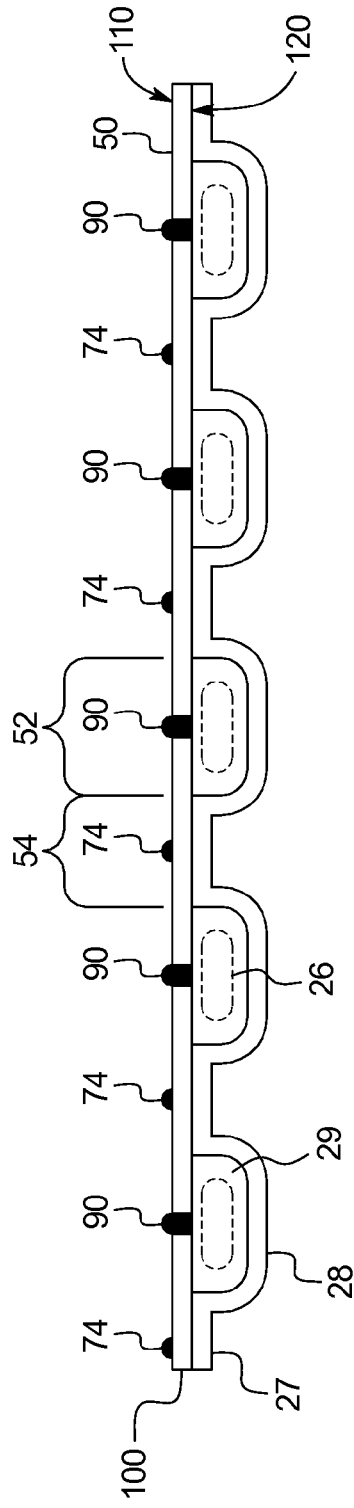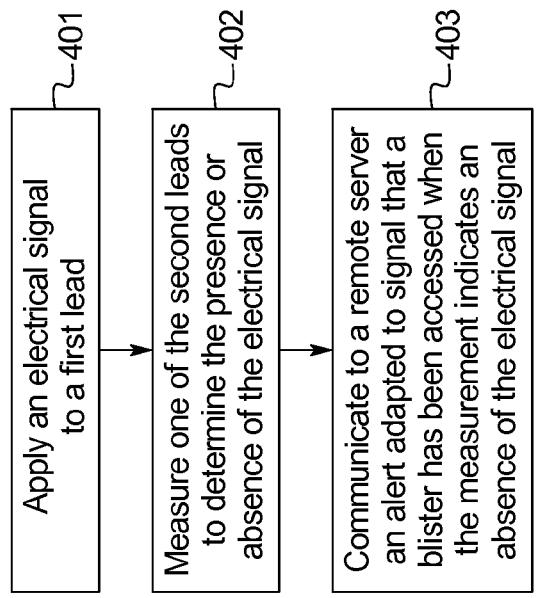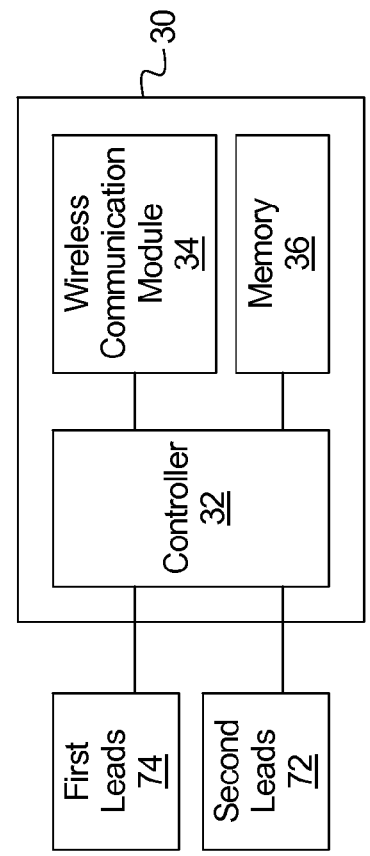

CONDUCTIVE GRID SENSOR FOR SMART PACKAGING

CROSS-REFERENCE TO RELATED APPLICATIONS

This application incorporates by reference and claims the benefit of priority to U.S. Provisional Application 61/939,108, filed on Feb. 12, 2014.

BACKGROUND OF THE INVENTION

The present subject matter relates generally to a system for remote unit-dose monitoring of prescription medicine. More specifically, the present invention relates to remote unit-dose monitoring of a blister packaging for medicaments.

Monitoring devices have become increasingly common for remote inventory control and remote status-awareness of products with characteristics such as high commercial value or safety concerns. Any prescribed medication classified as a Controlled Substance is an example of a product with both high street value and safety concerns. Examples of sensing devices for monitoring prescription medications are found in these publications, the entirety of each is incorporated by reference: U.S. Patent Application Publication No. 2013/0285681 A1, U.S. Pat. No. 7,178,417, U.S. Pat. No. 7,113,101, and U.S. Pat. No. 6,244,462. In order to enjoy broad utilization in high-volume applications such as routine medical care, monitoring devices must have very low complexity and costs.

The high street value and the highly addictive nature of Controlled Substances merit the use of unit-dose monitoring of each and every dose rather than the collection of less-informative data such as bottle open-and-close cycles. Unit-dose monitoring requires each dosage unit (i.e., each pharmaceutical pill, capsule, tablet, etc.) to be packaged individually with a means to remotely monitor for the presence or absence of each dose. Unit-dose monitoring may be accomplished with blister packaging, such as those described in the publications listed above that combine a blister shell with a means to monitor the removal of individual doses. Blister shells are product receptacles or product cavities within which individual doses are placed. In monitoring devices commercialized to date, the individual circuit paths are aligned with or affixed to medication blisters so that they correspond to a single blister or product receptacle, and the action of pressing against the product receptacle causes the product to pierce engineered failure points (weakened by, for example, die cutting) causing the disruption of the single corresponding circuit path.

In part because of limitations of circuitry approaches used to date, the applications of pharmaceutical unit-dose monitoring have not found widespread commercial use, but instead have been limited to serving small markets such as the monitoring of medications in clinical trial investigations sponsored by pharmaceutical companies. As a single example only, FIG. 13 of U.S. Patent Application Publication No. 2013/0285681 A1 shows the following limitations caused by the simple approaches in use to date: A) the complexity and number of conductive leads required to monitor just twelve doses shows that this approach would lead to very large packaging dimensions if expanded to monitor normally dispensed numbers of doses such as a one-month supply, for example; B) the complexity of the connection between the sensing leads and the monitoring electronics becomes very complex even when only moderate numbers of doses are monitored. For the purpose of this document, the simple circuitry approaches commercialized to date are termed "trace loops" because the monitoring of a single product receptacle requires a conductive loop that is dedicated to the receptacle plus a shared return conductor. In the example shown at FIG. 13 of U.S. Patent Application Publication No. 2013/0285681 A1, the monitoring of ten doses requires twelve dedicated leads combined with one shared conductor, so the connector must accommodate a total of thirteen conductive leads. As a further burden on the patient, FIG. 13 of U.S. Patent Application Publication No. 2013/0285681 A1 shows that the size of the packaging is dictated by the number of trace loops rather than by the size of the product being monitored. Product density, the number of products being monitored per unit of surface area, decreases rapidly with the trace-loop approach when clinically meaningful numbers of dosage units are monitored. Trace-loop circuitry approaches have been commercialized in the clinical-trials market to date because, contrary to routine medical care, people are typically paid to participate and are tightly monitored by the trial sponsor, so cumbersome packaging solutions are tolerated. These and other long-established shortcomings of commercialized approaches have been outlined in U.S. Pat. No. 7,178,417 (Column 1, Line 63 through Column 2, Line 7). Thus, because in-pharmacy assembly of smart packaging necessitates simple, robust, easy to use, and inexpensive connectors and because patients will not tolerate oversize packaging, a trace-loop approach cannot scale to monitor clinically meaningful quantities of doses.

New and high-volume applications for medication monitoring will tolerate neither excessive packaging dimensions nor connector expense and complexity associated with current sensing approaches. For example, drug-safety packaging is being tested to determine whether objective data collected from the packaging may be used to slow the crisis of prescription drug abuse, trafficking, and attendant beneficiary fraud (www.divert-x.com). Because patients using this system are not paid (as in clinical trials) and are not monitored via vigorous, ongoing person-to-person interaction (as in clinical trials), large devices that are expensive and difficult to assemble would not be accepted in the marketplace. As a further complication, the Divert-X and competing hardware rely on monitoring electronics and product packaging that are combined through a connector to form the completed smart packaging. In the case of Divert-X, the packaging is assembled in retail pharmacies; given the time constraints of this environment, the connector must be simple, robust, easy to use, and inexpensive.

In order to attempt to resolve some of these issues, Petersen, et al. revealed a conductive grid sensing approach in U.S. Pat. No. 7,113,101 (the '101 patent). This art proposes a fine mesh-like, electrically-conductive grid that is used to cover the blister openings and the medication. The grid is made of sets of electrically-conductive leads originating on the X- and Y-axes that intersect at right angles, analogous to the appearance of graph paper. The spacing between individual leads and intersections is considerably smaller than between leads in commercially manufactured sensing products such that each product cavity will overlay several leads and intersections. Because several leads will intersect each blister opening in the '101 patent, each dose-removal event will be sensed by the permanent disruption of several intersecting leads. The working theory of the '101 patent is that the removal of a plurality of doses may be sensed and accounted for by monitoring "a change in the resistance of the circuit."

The working theory of the '101 patent cannot be placed into practice for smart-blister packaging and, hence, this approach has not been commercialized. Specifically, the conductive grid design of the '101 patent cannot meet the aims of a compact, commercially-acceptable sensing packaging because of a technical problem we call "blinding." Blinding is the loss of inventory or status data obtainable from the packaging. Blinding occurs because the sensing conductive grid is permanently changed by physical removal of conductive grid material resulting from dose removal from the packaging. Specifically, the action of pressing against the product receptacle causes the dose to pierce failure points engineered into the conductive grid, allowing the removal of the dose from the packaging. Consider a conductive grid such as that taught in the '101 patent affixed to a blister package for the purpose of monitoring an inventory of 25 medication doses arranged in a square of 5 rows and 5 columns. Removal of a dose at each end of a single row blinds the monitoring device for all doses on the same row. As additional doses are removed, the device becomes blinded to the point where no system may sense additional dosing events and no accurate inventory reporting is possible.

Accordingly, there is a need for a system of remote unit-dose monitoring that overcomes the problems of circuit crowding, low product density, blinding, and excessively complex and expensive connectors, as described herein.

BRIEF SUMMARY OF THE INVENTION

To meet the needs described above and others, the present disclosure provides a remote unit-dose monitoring system utilizing conductive grid sensing that overcomes the blinding problem by using matrix addressing to make each dose individually addressable.

Matrix addressing operates by using row-and-column leads that permit each pairing of a row lead and a column lead to address a specific dosage. To motivate this approach, consider that despite the blinding problem, a conductive grid comprised of leads intersecting at right angles is an attractive approach when the number of connector leads needed to monitor all product receptacles is considered. In a five-by-five blister example, the connector need only accommodate ten leads when a conductive grid is used, whereas if the trace-loop approach is used than at least twenty-six leads are required. To carry the example further, if the blister is a seven-by-seven configuration (forty-nine doses), then the connector need only accommodate fourteen leads when a conductive grid is used, compared to the no fewer than fifty leads are needed if the trace-loop approach is used. The efficiency and scalability of the conductive grid approach is due to the fact that it does not require that each lead be dedicated to one product receptacle.

Specifically, matrix addressing may operate to determine whether a dose has been consumed by the probing (for example, in an embodiment, by applying a voltage) individual leads of a fine mesh-like conductive grid on one axis followed by measuring an endpoint (as examples: voltage change, presence or absence of a current, etc.) on all leads of the orthogonal axis of the two-dimensional conductive grid. As the electronic controls rapidly step and cycle through all the individual leads of the row axis and measure endpoints on the column axis, the presence or absence of a complete circuit may be determined. If a complete circuit is detected, then it may be inferred that a particular dose is unused, and likewise, if a complete circuit is not detected, then it may be inferred that a particular dose is used.

However, despite the benefits of matrix addressing, the blinding problem may still cause the failure of unit-dose monitoring after a number of doses are removed. The remote unit-does monitoring system of the present invention overcomes the blinding problem by offsetting the leads from the blister using stems such that the integrity of the leads is not compromised when a blister is opened. Each blister may be monitored by one or more stems electrically attached to the leads that may be compromised by the opening of a blister without compromising the integrity of the entire lead.

In an embodiment, an example remote unit-dose monitoring system may include a five-by-five dosage blister package and a monitoring device. The blister package may include various product doses. To monitor the dosages, a matrix may be provided that communicates via a simplified connector with a monitoring device.

The blister package may include a blister card and a backing. The blister card may be a thermoformed plastic shell with an array of cavities for each dose. The backing may include a substrate that is brittle to allow the dosage to be pushed through the backing for use.

The matrix may include orthogonal row leads and column leads intersecting at right angles wherein all leads are separate and electrically insulated from one another. Leads need not be at true ninety-degree angles; smaller angles of intersection are functional and appropriate for use in this application. The required insulation may be achieved by applying the conductive leads to opposite sides of a single sheet of non-conductive substrate or to separate sheets of substrate that are assembled in a later step.

In order to form a conductive circuit to monitor each dose, the column leads and row leads are electrically connected by stems. A stem may be a conductive appendage corresponding to each dose compartment that is in electrical contact with its corresponding lead and may extend over the dose compartment. The full length of every stem may be optionally insulated from stems belonging to orthogonal leads via any of the insulation approaches listed above. For each product cavity, a row stem and a column stem may be provided.

In order to complete the circuit between a row stem and column stem, a conductive zone may be provided to connect to the distal end of each pair of row stems and column stems. The conductive zone may pass through the substrate of the backing to create a conductive path from a column lead to a row lead via the row stem and column stem. It is contemplated that each conductive zone may correspond to one or a plurality of product cavities. If the leads have been applied to opposite sides of a single sheet of substrate, then the conductive zones may be established via through-hole contact wherein a hole or holes are cut in the substrate prior to applying conductive materials sufficient to ensure through-hole conductivity. If conductive materials have been applied to two sheets of substrate, then the conductive zones may be prepared by, for example, applying heat or pressure only to the conductive zone area to selectively bond together substrate and conductor.

In an embodiment, a remote unit-dose monitoring system includes a blister card including a plurality of flexible blisters; and a backing sheet including blister backing portions and backing securing portions, wherein when the backing securing portions are secured to the blister card, the blister backing portions are aligned opposite each blister forming a plurality of compartments adapted to store a medicament, and wherein the backing includes two or more conductive first leads affixed to the backing, two or more conductive second leads affixed to the backing, and a plurality of conductive zones, wherein each conductive zone electrically connects one of the first leads to one of the second leads, and wherein each blister backing portion includes a conductive zone.

In some embodiments, each conductive zone connects only to one of the first leads, and wherein each conductive zone connects only to one of the second leads. Additionally, in some embodiments, the blister backing portions do not include the first leads and the second leads. Moreover, in some embodiments, the remote unit-dose monitoring system further includes a plurality of first stems and second stems, wherein each of the first stems extends from one of the first leads onto one of the blister backing portions to connect with one of the conductive zones, and wherein each of the second stems extends from one of the second leads onto a one of the blister backing portions to connect with one of the conductive zones.

To provide matrix addressing, in some embodiment, the first leads are affixed to the backing at a transverse angle to the second leads. And, in some embodiments, the backing includes a first side and a second side, wherein the first leads are affixed on the first side, and the second leads are affixed on the second side, and wherein the conductive zone passes through the backing from the first side to the second side.

To track dosage use, in some embodiments the remote unit-dose monitoring system, further includes a controller electrically connected to the first leads and second leads, a wireless communications module in communication with the controller, and a memory in communication with the controller, wherein the memory includes stored instructions that, when executed by the controller, cause the controller to: apply an electrical signal to one of the first leads; measure one of the second leads to determine the presence or absence of the electrical signal; and communicate to a remote server an alert adapted to signal that a blister has been accessed when the measurement indicates an absence of the electrical signal.

In an embodiment, a method for tracking the use of medication includes the steps of: providing a remote unit-dose monitoring system including a controller, a wireless communications module in communication with the controller, a memory in communication with the controller, a blister card including flexible blisters, and a backing sheet including blister backing portions and backing securing portions, wherein when the backing securing portions are secured to the blister card, the blister backing portions are aligned to each blister forming a plurality of compartments adapted to store a medicament, and wherein the backing includes two or more conductive first leads affixed to the backing, wherein the first leads are electrically connected to the controller, two or more conductive second leads affixed to the backing, wherein the second leads are electrically connected to the controller, and a plurality of conductive zones, wherein each conductive zone electrically connects one of the first leads to one of the second leads, and wherein each blister backing portion includes a conductive zone; applying, via the controller, an electrical signal to one of the first leads; measuring, via the controller, one of the second leads to determine the presence or absence of the electrical signal; and communicating to a remote server an alert adapted to signal that a blister has been accessed when the measurement indicates an absence of the electrical signal.

In some embodiments of the method, each conductive zone connects only to one of the first leads, and wherein each conductive zone connects only to one of the second leads. And, in some embodiments of the method, the blister backing portions do not include the first leads and the second leads. Additionally, in some embodiments of the method, the remote unit-dose monitoring system further includes a plurality of first stems and second stems, wherein each of the first stems extends from one of the first leads onto one of the blister backing portions to connect with one of the conductive zones, and wherein each of the second stems extends from one of the second leads onto a one of the blister backing portions to connect with one of the conductive zones.

In some embodiments of the method, the first leads are affixed to the backing at a transverse angle to the second leads. Additionally, in some embodiments of the method, the backing includes a first side and a second side, wherein the first leads are affixed on the first side, and the second leads are affixed on the second side.

In an embodiment, a remote unit-dose monitoring system includes: a blister card including a plurality of flexible blisters; and a backing sheet including blister backing portions and backing securing portions, wherein when the backing securing portions are secured to the blister card, the blister backing portions are aligned to each blister forming a plurality of compartments adapted to store a medicament, wherein the backing includes a first side and a second side, and wherein the backing includes two or more conductive first leads affixed to the backing, wherein the first leads are affixed on the first side, two or more conductive second leads affixed to the backing, wherein the second leads are affixed on the second side, and a plurality of conductive zones, wherein each conductive zone electrically connects one of the first leads to one of the second leads, wherein each blister backing portion includes a conductive zone, and wherein each conductive zone connects only to one of the first leads, and wherein each conductive zone connects only to one of the second leads.

In some embodiments, the blister backing portions do not include the first leads and the second leads. And in some embodiments, the remote unit-dose monitoring system further includes a plurality of first stems and second stems, wherein each of the first stems extends from one of the first leads onto one of the blister backing portions to connect with one of the conductive zones, and wherein each of the second stems extends from one of the second leads onto a one of the blister backing portions to connect with one of the conductive zones. Additionally, in some embodiments, the first leads are affixed to the backing at a transverse angle to the second leads. Moreover, in some embodiments, the backing includes a first side and a second side, wherein the first leads are affixed on the first side, and the second leads are affixed on the second side. Further, in some embodiments, the remote unit-dose monitoring system further includes a controller, a wireless communications module in communication with the controller, and a memory in communication with the controller, wherein the memory includes stored instructions that, when executed by the controller, cause the controller to: apply an electrical signal to one of the first leads; measure one of the second leads to determine the presence or absence of the electrical signal; communicate to a remote server an alert adapted to signal that a blister has been accessed when the measurement indicates an absence of the electrical signal.

An object of the invention is to provide a solution to the problem of unit-dose monitoring of each and every dose of a controlled substance.

Another object of the invention is to provide unit-dose monitoring that is not dependent on single lead path per blister solutions that causes circuit crowding and low product density.

Yet another object of the invention is to provide a solution to the blinding problem in previous approaches to remote unit-dose monitoring using blister packaging including a conductive grid.

Yet a further object of the invention is to provide unit-dose monitoring using simple and inexpensive connectors.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 2 is a cross-sectional side view of the blister package of the remote unit-dose monitoring system of FIG. 1.

FIG. 3 is logical diagram illustrating the electrical components of the remote unit-dose monitoring system of FIG. 1.

FIG. 4 is a flowchart illustrating the steps of a remote unit-dose monitoring method performed by the remote unit-dose monitoring system.

DETAILED DESCRIPTION OF THE INVENTION

Figure 1:
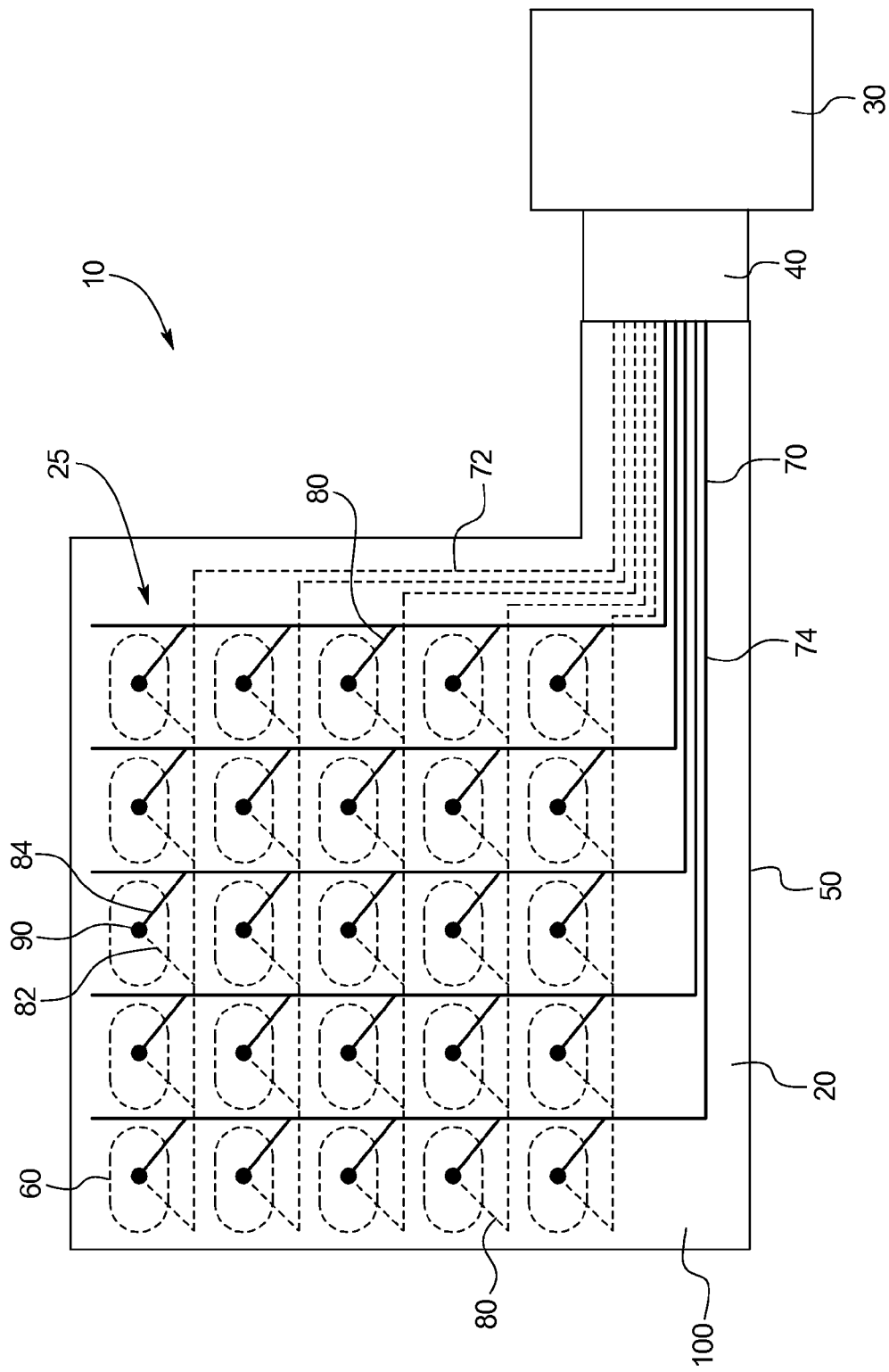
FIG. 1 is a schematic representation of a remote unit-dose monitoring system of the present invention.

FIGS. 1 and 2 illustrate an example of a remote unit-dose monitoring system 10 including a five-by-five dosage blister package 20 and a monitoring device 30. As shown, the blister package 20 includes various doses 60. To monitor the doses 60, a matrix 25 is provided that communicates via a simplified connector 40 with the monitoring device 30. The simplified connector 40 may afford a robust, inexpensive, and easy-to-use connection between the conductors of the matrix 25 and the monitoring device 30. It is contemplated that a blister package 20 may be a single-use item made of inexpensive materials and that a single monitoring device 30 may be used with multiple blister packages 20 by replacing each blister package 20 after all of the doses 60 have been emptied.

The blister package 20 may include a blister card 27 and a backing 50. The blister card 27 may be a thermoformed plastic shell with an array of blisters 28 that define the shape of compartments 29 for each dose 60 of medicament 26. The backing 50 may include a substrate 100 that is brittle to allow the dosage 60 to be pushed through the backing 50 for use. In FIG. 1, the backing 50 obscures the blister card 27.

The backing 50 may be a sheet including blister backing portions 52 and backing securing portions 54. The blister securing portions 54 may secure the backing 50 to the blister card 27, for example, the backing 50 may be glued or otherwise strongly attached to the blister card 27 at the blister securing portions 54. Conversely, each blister backing portion 52 is aligned to one of the blisters 28 such that the blister 28 and the blister backing portion 52 form a compartment 29 for storing a medicament 26.

As shown, the matrix 25 may be composed of an array of leads 70. In the embodiment shown, the matrix 25 includes orthogonal row leads 72 and column leads 74 intersecting at right angles wherein all leads 70 are separate and electrically insulated from one another. Leads 70 need not be at true ninety-degree angles; smaller angles of intersection are functional and appropriate for use in this application. The row leads 72 may be electrically insulated from the column leads 74 by applying the conductive leads 70 to opposite sides of a single sheet of non-conductive substrate 100 or to separate sheets of substrate 100 that are assembled to form a single substrate 100. Alternatively, the row leads 72 and column leads 74 may be attached on the same side of the backing 50 while being separated by an insulating layer.

In the example shown in FIG. 1, solid lines represent column leads 74 that may be applied to a first side 110 of a single sheet of non-conductive substrate 100, while dashed lines represent row leads 72 that may applied to the opposite second side 120 of the substrate 100. It is contemplated that column leads 74 and row leads 72 may be applied to either side of the substrate 100, including both on the same side. For clarity, the portions of the leads 70 that approach and touch the connector 40 are shown individually in FIG. 1. In a preferred embodiment, the column leads 74 may be superimposed over the row leads 72 (but on opposite sides of the substrate 100)—hence forming a two-sided connection of minimum width.

The substrate 100 of the backing 50 may be manufactured from any appropriate material that is both non-conductive and to which conductive materials such as inks or metallic films may be applied with needed accuracy. If separate sheets are used to form a single substrate 100, then the sheets may be oriented so that the conductive leads 70 are not in electrical contact; with a face-to-face orientation, non-conductive coatings or a separating sheet of non-conductive material or any other approach may be used to ensure that the leads 70 are not in electrical contact. The leads 70 may be made by depositing patterned conductive inks, films, or other patternable material on the substrate 100.

In order to complete the circuit between a row lead 72 and column lead 74, a conductive zone 90 may be provided to connect each pair of row leads 72 and column leads 74. FIG. 1 shows the positioning of conductive zones 90 represented as darkened circles. It is contemplated that each conductive zone 90 may correspond to one or a plurality of doses 60. If the leads 70 have been applied to opposite sides of a single sheet of substrate 100, then the conductive zones 90 may be established via through-hole contact wherein a hole or holes are cut in the substrate 100 prior to applying conductive materials. If conductive materials have been applied to two sheets of substrate 100, then the conductive zones 90 may be prepared by, for example, applying heat, chemical treatment, or pressure only to the conductive zone area to selectively bond together substrate and conductor.

In order to form a conductive circuit to monitor each dose 60, the column leads 74 and row leads 72 are electrically connected to the conductive zones 90 by stems 80. The stems 80 may be a conductive appendage corresponding to each dose 60 that is in electrical contact with its corresponding leads 70 and may extend over the compartment 29. For example, for each blister backing portions 52, a row stem 82 and a column stem 84 may be provided. The conductive zone 90 may passes through the substrate 100 to create a conductive path from a column lead 74 to a row lead 72 via the row stem 82 and column stem 84. The full length of every row stem 82 may be insulated from column stems 84 as described above for insulating leads 70.

As shown in FIG. 1, a continuous conductive path begins at a row lead 72 on one side of a substrate, and passes through the corresponding row stem 82, through the conductive zone 90, through column stem 84 on the opposite side, and finally ends at the column lead 74 on the opposite side of the substrate 100. When a dose 60 is removed from the compartments 29 by pushing the medicament 26 through the substrate 100, the continuous conductive path may be broken. For example, removal of a dose 60 may physically remove one of the conductive zones 90 from the matrix 25 by way of engineered failure points surrounding the conductive zone 90. Still, the removal of the conductive zone 90 may disrupt a single conductive path while leaving all other paths intact. When the conductive zone 90 is separated from the leads 70 by use of stems 80, the leads 70 remain intact and the matrix 25 does not suffer from blinding. Using the conductive grid approach of the present disclosure, product density is maximized and connector complexity is minimized.

FIGS. 1 and 2 are not intended to suggest particular manufacturing steps but rather are meant to explain one example of a preferred embodiment of the invention. In a preferred embodiment, conductive materials for leads 70, stems 80, and conductive zones 90 are applied to the substrate 100 in as few manufacturing steps as possible. For example, in the case of a single-sheet substrate 100 with conductive materials applied to both sides and employing through-hole conduction, preference is given to a roll-to-roll process where all features are applied in a single manufacturing step. Although the conductive grid examples described herein are square in shape (a 5×5 matrix, for example), other arrangements of product compartments 29 and the matrix 25 are possible. For example, a rectangular grid would allow a large number of doses 60 to be monitored, with the blister packages 20 dispensed in roll form to save space.

Turning to FIGS. 3 and 4, FIG. 3 illustrates the electrical components of an embodiment of the remote unit-dose monitoring system 10, and FIG. 4 is a flowchart illustrating the steps of a remote unit-dose monitoring method 400 performed by the remote unit-dose monitoring system 10. In an embodiment, a controller 32 of the remote unit-dose monitoring system 10 may carry out the method 400. A memory 36 may include instructions that are executed by the controller 32 to cause the controller 32 to carry out the method 400. As shown in FIG. 4, the remote unit-dose monitoring method 400 may include the steps of: at step 401, apply an electrical signal to a first lead; at step 402, measure step-wise each of a plurality of second leads to determine the presence or absence of the electrical signal; and at step 403, communicate to a remote server an alert adapted to signal that a blister has been accessed when the measurement indicates an absence of the electrical signal. The alert may be communicated to the remote server via a wireless communications module 34. In some embodiments, the remote unit-dose monitoring method 400 may be performed by a healthcare organization and include the further step of providing a remote unit-dose monitoring system 10 to a patient.

It should be noted that various changes and modifications to the presently preferred embodiments described herein will be apparent to those skilled in the art. Such changes and modifications may be made without departing from the spirit and scope of the present invention and without diminishing its attendant advantages.

I claim:

1. A remote unit-dose monitoring system comprising:
a blister card including a plurality of flexible blisters; and
a backing sheet including blister backing portions and backing securing portions, wherein when the backing securing portions are secured to the blister card, the blister backing portions are aligned to each of the flexible blisters, forming a plurality of compartments adapted to store a medicament, and wherein the backing sheet includes:
two or more conductive first leads affixed to the backing sheet;
two or more conductive second leads affixed to the backing sheet; and
a plurality of conductive zones, wherein each conductive zone of the plurality of conductive zones electrically connects one of the first leads to one of the second leads, and wherein each of the blister backing portions includes the conductive zone.

2. The remote unit-dose monitoring system of claim 1, wherein each conductive zone connects to only one of the first leads, and wherein each conductive zone connects to only one of the second leads.

3. The remote unit-dose monitoring system of claim 1, wherein the blister backing portions do not include the first leads and the second leads.

4. The remote unit-dose monitoring system of claim 3, further including a plurality of first stems and second stems, wherein each of the first stems extends from one of the first leads onto one of the blister backing portions to connect with one of the conductive zones, and wherein each of the second stems extends from one of the second leads onto a one of the blister backing portions to connect with one of the conductive zones.

5. The remote unit-dose monitoring system of claim 1, wherein the first leads are affixed to the backing sheet at a transverse angle to the second leads.

6. The remote unit-dose monitoring system of claim 1, wherein the backing sheet includes a first side and a second side, wherein the first leads are affixed on the first side, and the second leads are affixed on the second side, and wherein the conductive zone passes through the backing from the first side to the second side.

7. The remote unit-dose monitoring system of claim 1, further including a controller electrically connected to the first leads and second leads, a wireless communications module in communication with the controller, and a memory in communication with the controller, wherein the memory includes stored instructions that, when executed by the controller, cause the controller to:
apply an electrical signal to one of the first leads;
measure one of the second leads to determine the presence or absence of the electrical signal; and
communicate to a remote server an alert adapted to signal that a blister has been accessed when the measurement indicates an absence of the electrical signal.

8. The remote unit-dose monitoring system of claim 1, wherein the backing includes a first side and a second side, wherein the first leads are affixed on the first side, and the second leads are affixed on the second side.

9. A method for tracking the use of medication, comprising:
providing a remote unit-dose monitoring system including;
a controller,
a wireless communications module in communication with the controller, a memory in communication with the controller,
a blister card including a plurality of flexible blisters, and
a backing sheet including blister backing portions and backing securing portions, wherein when the backing securing portions are secured to the blister card, the blister backing portions are aligned to each blister forming a plurality of compartments adapted to store a medicament, and wherein backing sheet includes:
  two or more conductive first leads affixed to the backing sheet, wherein the first leads are electrically connected to the controller;
  two or more conductive second leads affixed to the backing sheet, wherein the second leads are electrically connected to the controller; and
  a plurality of conductive zones, wherein each of the plurality of conductive zones electrically connects one of the first leads to one of the second leads, and wherein each of the blister backing portions includes a conductive zone;
applying, via the controller, an electrical signal to one of the first leads;
measuring, via the controller, one of the second leads to determine the presence or absence of the electrical signal;
when the measurement indicates an absence of the electrical signal, communicating to a remote server an alert adapted to signal that a blister has been accessed.

10. The method of claim 9, wherein each conductive zone connects only to one of the first leads, and wherein each conductive zone connects only to one of the second leads.

11. The method of claim 9, wherein the blister backing portions do not include the first leads and the second leads.

12. The method of claim 11, wherein the remote unit-dose monitoring system further includes a plurality of first stems and second stems, wherein each of the first stems extends from one of the first leads onto one of the blister backing portions to connect with one of the conductive zones, and wherein each of the second stems extends from one of the second leads onto a one of the blister backing portions to connect with one of the conductive zones.

13. The method of claim 9, wherein the first leads are affixed to the backing sheet at a transverse angle to the second leads.

14. The method of claim 9, wherein the backing sheet includes a first side and a second side, wherein the first leads are affixed on the first side, and the second leads are affixed on the second side.

15. A remote unit-dose monitoring system comprising:
a blister card including a plurality of flexible blisters; and
a backing sheet including blister backing portions and backing securing portions, wherein when the backing securing portions are secured to the blister card, the blister backing portions are aligned to each blister forming a plurality of compartments adapted to store a medicament, wherein the backing sheet includes a first side and a second side, and wherein the backing sheet further includes:
  two or more conductive first leads affixed to the backing, wherein the first leads are affixed on the first side;
  two or more conductive second leads affixed to the backing sheet, wherein the second leads are affixed on the second side; and
  a plurality of conductive zones, wherein each of the conductive zones electrically connects one of the first leads to one of the second leads, wherein each blister backing portion includes a conductive zone, and wherein each conductive zone connects only to one of the first leads, and wherein each conductive zone connects only to one of the second leads.

16. The remote unit-dose monitoring system of claim 15, wherein the blister backing portions do not include the first leads and the second leads.

17. The remote unit-dose monitoring system of claim 15, further including a plurality of first stems and second stems, wherein each of the first stems extends from one of the first leads onto one of the blister backing portions to connect with one of the conductive zones, and wherein each of the second stems extends from one of the second leads onto a one of the blister backing portions to connect with one of the conductive zones.

18. The remote unit-dose monitoring system of claim 15, wherein the first leads are affixed to the backing at a transverse angle to the second leads.

19. The remote unit-dose monitoring system of claim 15, further including a controller, a wireless communications module in communication with the controller, and a memory in communication with the controller, wherein the memory includes stored instructions that, when executed by the controller, cause the controller to:
  apply an electrical signal to one of the first leads;
  measure one of the second leads to determine the presence or absence of the electrical signal;
  communicate to a remote server an alert adapted to signal that a blister has been accessed when the measurement indicates an absence of the electrical signal.

* * * * *